US008815136B2

(12) United States Patent
Sgaravatto et al.

(10) Patent No.: US 8,815,136 B2
(45) Date of Patent: Aug. 26, 2014

(54) METHOD FOR THE PRODUCTION OF BODIES IN PLASTIC MATERIAL COMPRISING AT LEAST TWO PORTIONS HINGED TO EACH OTHER BY A SINGLE ROTATION PIN

(75) Inventors: Roberto Sgaravatto, Padua (IT); Ulisse Chiarin, Padua (IT)

(73) Assignee: Meus S.r.l., Piove di Sacco, Padua (IT)

( * ) Notice: Subject to any disclaimer, the term of this patent is extended or adjusted under 35 U.S.C. 154(b) by 148 days.

(21) Appl. No.: 13/509,776

(22) PCT Filed: Oct. 18, 2010

(86) PCT No.: PCT/IB2010/054702
§ 371 (c)(1),
(2), (4) Date: May 14, 2012

(87) PCT Pub. No.: WO2011/064680
PCT Pub. Date: Jun. 3, 2011

(65) Prior Publication Data
US 2013/0015605 A1    Jan. 17, 2013

(30) Foreign Application Priority Data

Nov. 27, 2009    (IT) ................................. PD09A0359

(51) Int. Cl.
| | |
|---|---|
| *B29C 45/14* | (2006.01) |
| *B29C 45/00* | (2006.01) |
| *A61B 5/15* | (2006.01) |
| *A61B 5/153* | (2006.01) |
| *A61M 5/32* | (2006.01) |
| *B29L 31/00* | (2006.01) |

(52) U.S. Cl.
CPC ....... *B29C 45/006* (2013.01); *B29C 2045/0024* (2013.01); *A61B 5/1405* (2013.01); *A61B 5/153* (2013.01); *A61M 5/3216* (2013.01); *B29C 45/0017* (2013.01); *B29L 2031/753* (2013.01); *B29L 2031/7544* (2013.01)
USPC ........ 264/242; 264/163; 264/328.8; 425/577; 425/588

(58) Field of Classification Search
CPC .................. B29C 45/0017; B29C 2045/1601; B29C 2045/1635; B29C 2045/0065; B29C 2045/0067; B29C 2045/0068; B29C 2045/006; B29C 45/006; B29C 2045/0022; B29C 2045/0017; B29C 2045/0024
USPC ............ 264/163, 242, 328.7, 328.8; 425/577, 425/588
See application file for complete search history.

(56) References Cited

U.S. PATENT DOCUMENTS 3,443,005 A * 5/1969 Braun ........................... 264/245
3,456,913 A * 7/1969 Lutz ................................ 249/63
(Continued)

FOREIGN PATENT DOCUMENTS

| DE | 19757387 | 6/1999 |
|---|---|---|
| DE | 19757387 A1 * | 6/1999 |

(Continued)

OTHER PUBLICATIONS

Machine translation of German Patent Publication No. DE 19757387 A1, originally published Jun. 1999, 4 pages.*

*Primary Examiner* — William Bell
(74) *Attorney, Agent, or Firm* — Shoemaker and Mattare

(57) ABSTRACT

The present invention relates to a method for the production of bodies in plastic comprising two portions hinged to each other by a single rotation pin. The method comprises the steps: a) predisposing a mold with two distinct forming chambers for the two portions; the mold comprises a third chamber for the single pin, made and positioned in such a way that the pin is formed already aligned along the hinge axis; the mold is provided with a pair of pegs axially distanced from each other to form the third chamber and sliding along the axis between a first and a second operating position; b) positioning the pegs in the first position; c) injecting plastic material inside the chambers; d) shifting the pegs from the first to the second position, bringing the pin to engage inside the seats; e) opening the mold and extracting the two assembled portions.

20 Claims, 13 Drawing Sheets

(56) References Cited

U.S. PATENT DOCUMENTS

| | | | |
|---|---|---|---|
| 4,579,709 A * | 4/1986 | Ferreri | 264/242 |
| 4,641,701 A * | 2/1987 | Yamamoto | 164/90 |
| 5,207,653 A | 5/1993 | Janjua et al. | |
| 5,304,336 A * | 4/1994 | Karlsson et al. | 264/242 |
| 7,320,768 B2 * | 1/2008 | Eimura | 264/242 |
| 7,951,322 B2 * | 5/2011 | Clark | 264/328.8 |
| 2004/0210196 A1 * | 10/2004 | Bush, Jr. et al. | 604/192 |

FOREIGN PATENT DOCUMENTS

| | | |
|---|---|---|
| EP | 56671 | 7/1982 |
| EP | 995455 | 4/2000 |
| EP | 1346739 | 9/2003 |
| JP | 05245870 A * | 9/1993 |
| WO | 92/11802 | 7/1992 |

* cited by examiner

METHOD FOR THE PRODUCTION OF BODIES IN PLASTIC MATERIAL COMPRISING AT LEAST TWO PORTIONS HINGED TO EACH OTHER BY A SINGLE ROTATION PIN

FIELD OF THE INVENTION

The present invention relates to a method for the production of bodies in plastic material comprising at least two portions hinged to each other by a single rotation pin.

Advantageously, the method according to the invention can be used to make components destined for use in the clinical sphere, such as components of devices for taking blood samples.

In particular, the method according to the invention, can be used to make shields for protecting needles provided with a coupling collar hinged and associable to a vial holder, or to make needle holder stubs provided with hinged protective shields.

The present invention also concerns a mould for the injection of plastic material to form at least two portions hinged to each other by a single rotation pin, utilisable in particular to implement the method according to the invention.

BACKGROUND OF THE INVENTION

In the clinical field the need to take blood samples safely using needle devices provided with means offering the operator total shielding from the needle after taking the blood sample so as to prevent the risk of accidental contact with the needle itself is strongly felt.

One of the solutions proposed envisages providing the device for taking samples with a mobile protective shield which, mechanically connected to it in a stable manner, can be moved from a non active position, wherein it does not interfere with the needle, and an active position, wherein it encloses the needle within it, thereby shielding it.

A device of this type for taking samples is described, for example, in the European patent EP 56671 B1. The protective shield is connected to the device, in this case, a vial holder, by a flexible tongue H ("living hinge"; as shown in FIG. 1 hereto attached, extracted from EP 56671 B1).

A similar device for taking samples is described in the U.S. Pat. No. 5,207,653. The protective shield is connected to the device, in this case, a needle holder hub, by a hinge. In a first embodiment the screen is hinged to the hub by means of two pins P' which projecting from said shield snap-fit into two counter-shaped seats P''' made in the hub (as shown in FIG. 2, extracted from U.S. Pat. No. 5,207,653). In a second embodiment the shield is hinged to the hub by means of a single pin M housed in through seats made so as to be aligned on the hub and on the shield (as shown in FIG. 3, extracted from U.S. Pat. No. 5,207,653).

Yet another device is described in the European patent EP 995455 B1. The protective shield is connected to the device for taking samples, in this case, a needle holder hub, by a snap-coupling system. Such system is composed of a U-shaped hook, which, projecting from the needle-holder hub, defines the hinging seat with an open slot, and by a bar B, which projecting from the shield by means of two arms is aligned along the rotation axis and scaled to snap-fasten to the hook in a relation of free rotation acting as a pivot (as shown in FIG. 4, extracted from EP 995455 B1).

The solution described in the European patent EP 56671 B1 (device with flexible tongue) is simple to construct inasmuch as it does not require mechanical couplings of small parts. However this solution has operating limits linked to the fact that, as a result of the shape memory, the flexible tongue tends to resume its original position acquired at the moment of moulding.

This problem does not arise however in those solutions adopting a mechanical type joint.

Of the solutions with a mechanical type joint, the solution of patent EP 995455 B1 (device with snap-fasten, hook-bar system) and the first solution of the U.S. Pat. No. 5,207,653 (device with snap-fasten system composed of two pin-seat pairs, see FIG. 2) also have the advantage of being simple to produce from a constructional point of view. The two parts to be hinged can, in fact, be moulded separately and then subsequently easily assembled to each other.

The two solutions mentioned above are not, however, entirely operationally satisfactory, despite ensuring functionality in terms of safety in protecting the needle when the shield is in the active shielding position. This is due essentially to the fact that the structure of the mechanical joints used in these two solutions does not ensure a stable connection of the protective shield when the latter is in the non active position. In fact, in the case of lateral impact (i.e. directed parallel to the rotation axis of the shield) the shield may be pushed out of the hinging seat and thereby be disconnected from the device.

This happens, in particular, with the solution described in patent EP 995455 B1, i.e. with the device provided with a hook-bar fastening system. The hook defines a hinging seat open all along its axial extension. When the shield is positioned on the open side of the hook (in the non-active shielding position) the two support arms of the bar do not interfere laterally with the hook and cannot therefore prevent lateral shifts of the shield.

The mechanical type joint adopted in the second embodiment of the U.S. Pat. No. 5,207,653 (device with single hinge and through seats, see FIG. 3) ensures rather a stable connection of the shield to the device thanks to the presence of a single hinge extending all along the hinging axis.

This solution has the disadvantage however of being more complicated to produce in terms of construction than the other solutions with mechanical joints. The critical step is the assembly of the components. This operation is difficult not just on account of having to handle small parts (especially the pin), but also due to the fact that assembly of the hinge requires forcing the pin inside the through seats. The pin is in fact scaled to work with an interference relation at least with some sections of the through seats, the interference being essential to prevent the pin from accidentally coming out of the hinging seat and for the shield to rotate freely around the pin by gravity, under its own weight, thereby preventing normal use of the device.

SUMMARY OF THE INVENTION

Consequently, the purpose of the present invention is to overcome the drawbacks of the prior art described above, by making available a method for the production of bodies in plastic material comprising at least two portions hinged to each other by a single rotation pin, enabling production of a mechanically stable and efficacious hinging system simply and economically.

A further purpose of the present invention is to provide a mould for the injection moulding of plastic materials to implement the method according to the invention.

BRIEF DESCRIPTION OF THE DRAWINGS

The technical characteristics of the invention, in relation to the above purposes, can be seen clearly from the contents of the following claims and the advantages of the same will be more clearly comprehensible from the detailed description below, made with reference to the attached drawings, showing one or more embodiments by way of non-limiting examples, wherein:

DETAILED DESCRIPTION

The present invention relates to a method for the production of bodies in plastic material comprising at least two portions hinged to each other by a single rotation pin.

Advantageously, the method according to the invention, can be used to make components destined for use in the clinical sector, such as components of devices for taking blood samples.

In particular, the method according to the invention, can be used to produce, simply and economically, needle protection devices associable with vial holders (see FIGS. 9*a* and 9*b*) or protected needle holder devices associable with vial holders (see FIGS. 10*a* and 10*b*), comprising at least two portions 1 and 2, mechanically hinged to each other by a single pin 3, and having full operative functionality. Devices overcoming all the limitations of the prior art mentioned above are thereby obtained.

The present invention also concerns a mould for the injection of plastic material to form at least two portions 1 and 2 hinged to each other by a single rotation pin 3, utilisable in particular to implement the method according to the invention.

According to the general concept which the invention is based on, the portions 1 and 2 destined to be hinged together are assembled directly inside the mould. The (single) rotation pin 3 is formed and then-while still inside the mould, inserted in the hinge seats made in the aforesaid two portions 1 and 2.

The method thereby permits the simultaneous assembly and injection moulding of the single components.

According to a particularly advantageous aspect of the invention, which will be described in further detail below, the injection moulding of the single components and of the pin in particular has been designed to facilitate and speed-up contextual assembly of the parts.

The method according to the invention considerably simplifies the assembly of components (or portions) of a small size or in any case troublesome to handle.

In particular the method simplifies, or even permits, the assembly of components requiring the mechanical interference coupling of a number of small parts.

Thanks to the invention, it is no longer necessary to handle the single components but only the already assembled components. This simplifies the production process facilitating logistic management of the products.

According to a general form of application, the method according to the invention, comprises firstly the step a) of predisposing a suitable mould, the essential characteristics of which are described below.

The description of the essential and preferred characteristics of the mould according to the invention will be made with reference to the attached Figures showing an example of a mould specifically created to produce the device illustrated in FIG. 9*a*. The essential characteristics of the mould according to the invention are also maintained in a mould (not shown in the attached drawings) specifically created to produce the device illustrated in FIG. 10*a*.

Figure 11:
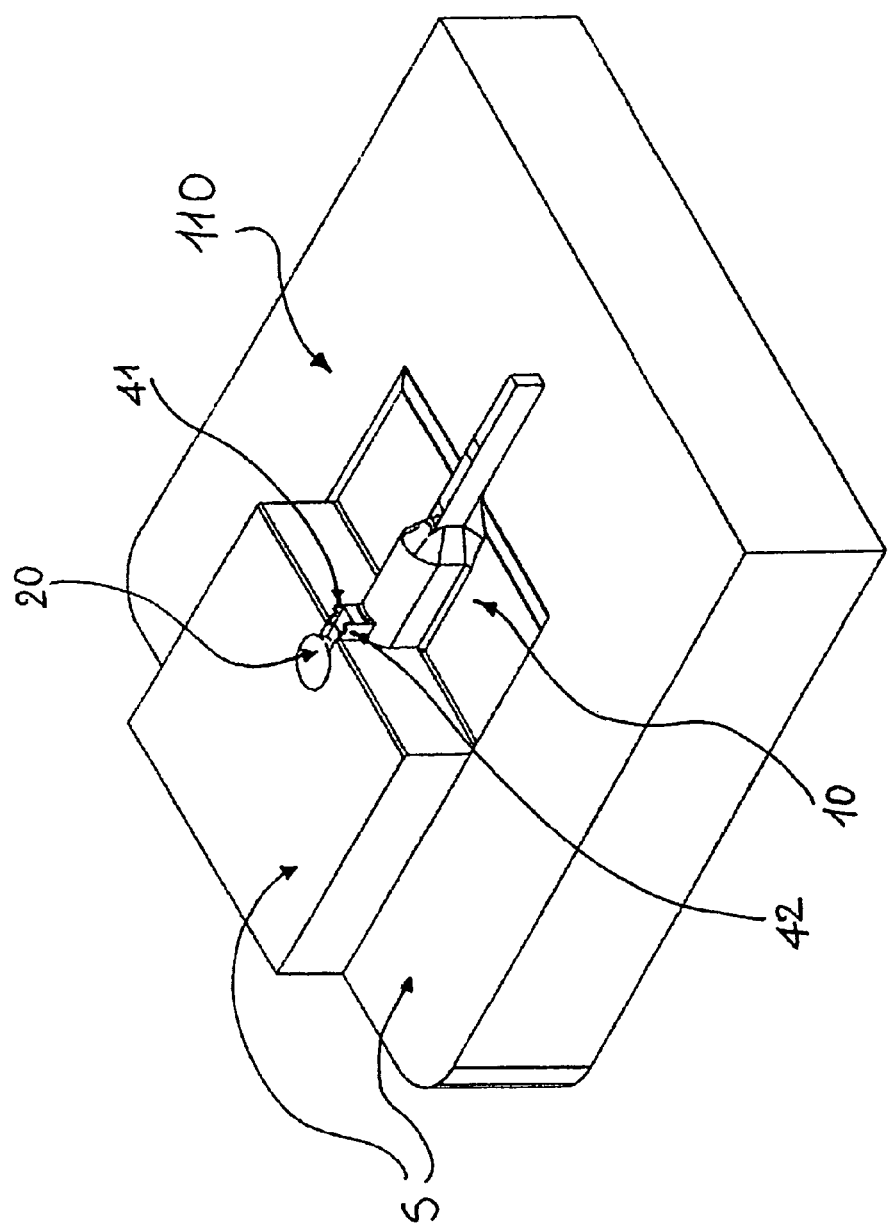
FIG. 11 shows the male half-mould of a mould made according to the invention and scaled specifically to make the shield and relative collar illustrated in FIG. 9*a*.
Figure 13:
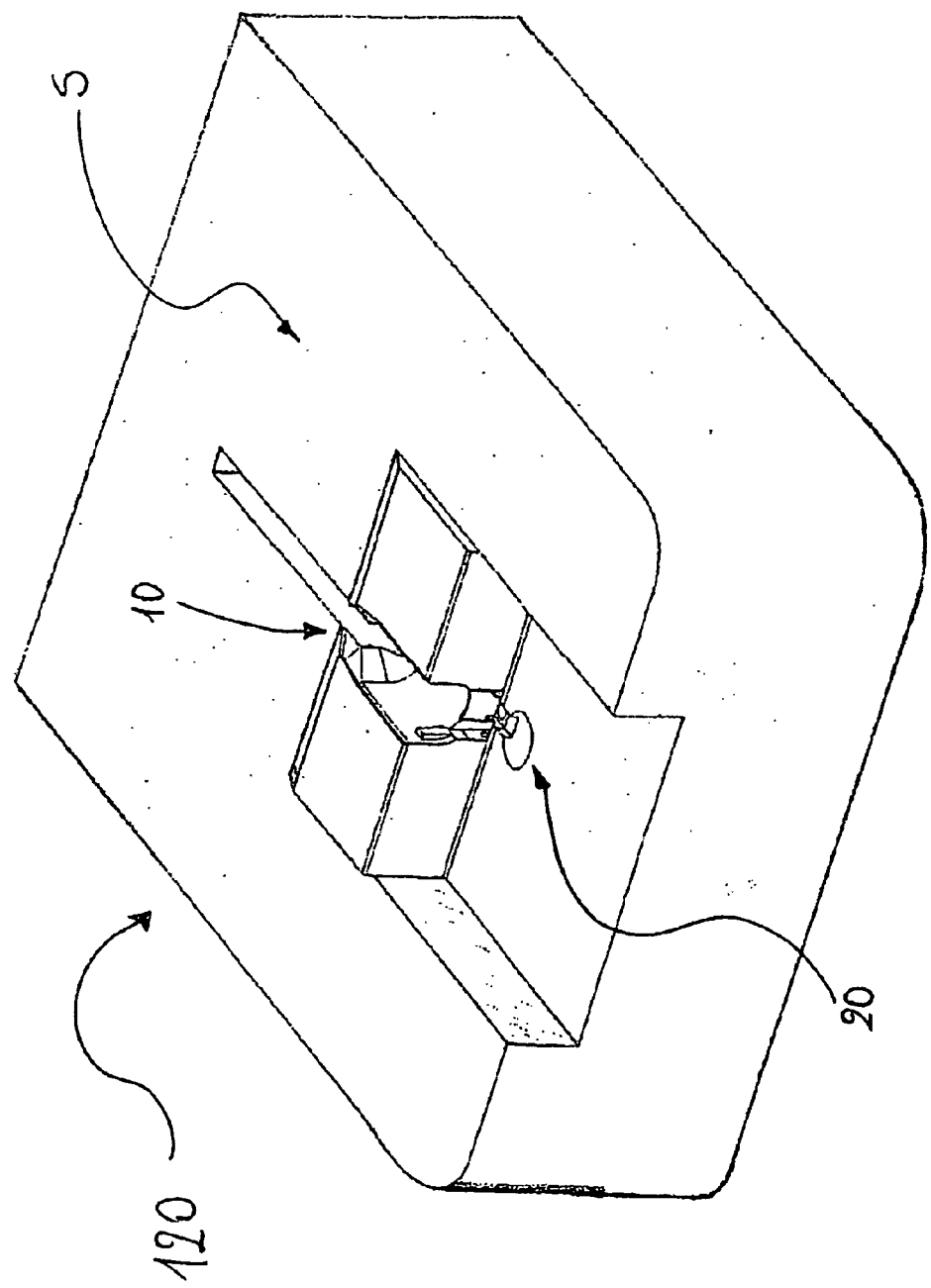
FIG. 13 shows the female half mould corresponding to the male half mould illustrated in FIG. 11.
Figure 15:
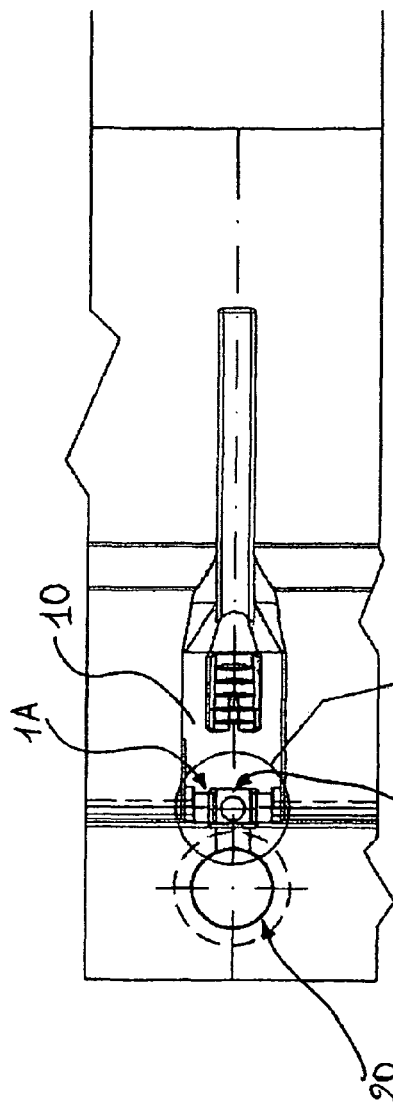
FIG. 15 shows a plan view of a detail of the half mould illustrated in FIG. 13 relative to forming chambers.

As may be seen, for example, in FIGS. 11, 13 and 15, the mould 100 is provided with at least two distinct forming chambers 10, 20 for moulding the aforesaid two portions 1,2, to be hinged to each other by the single pin 3.

Figure 6A:
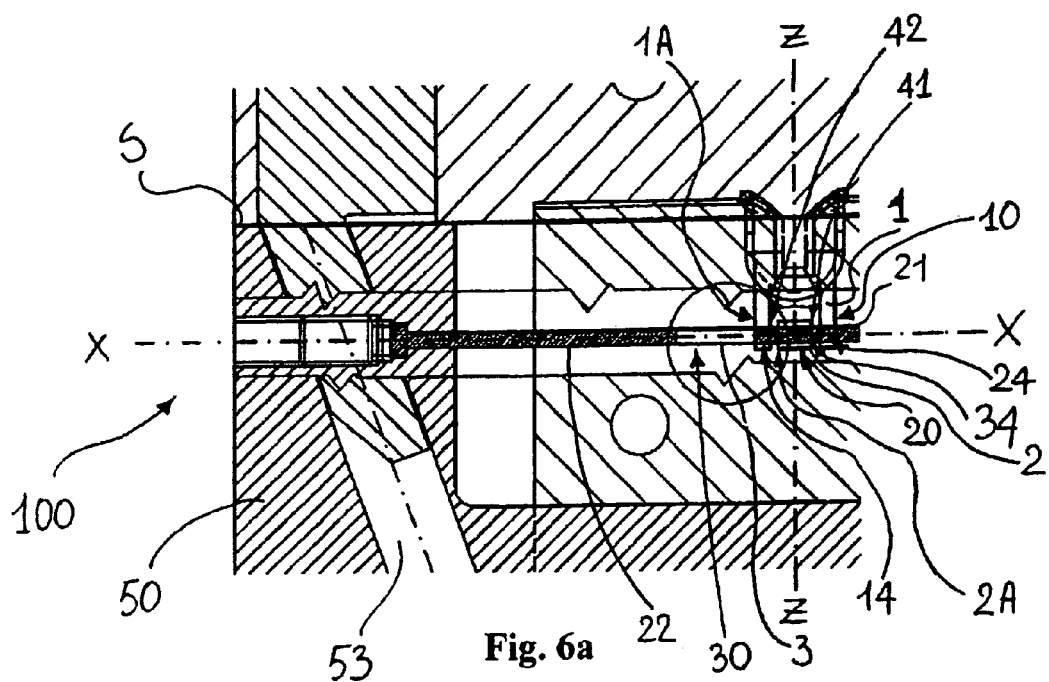
FIG. 6*a* shows a view of a detail of FIG. 5.

According to an essential aspect of the invention, as may be seen, for example, in FIG. 6*a*, the aforesaid two forming chambers 10 and 20 are shaped and reciprocally distanced in the mould 100 so that the two portions 1, 2 destined to be hinged, are formed in the mould already positioned in a position of reciprocal coupling, ready to be connected to each other along the hinge axis X by the single pin 3.

As will be explained further below, the first 10 and the second forming chamber 20 are distinct from each other in the sense that they are not fluidically communicating. It is, in fact, essential that at the end of the forming the two portions 1 and 2 are two separate and distinct bodies.

According to another essential aspect of the invention, the mould 100 comprises a third forming chamber 30 for the single pin 3, as may be seen for example in FIG. 6*a*.

Such third chamber 30 being made and positioned in the mould in such a way that the single pin 3 is formed already aligned along the hinge axis X.

Figure 2:
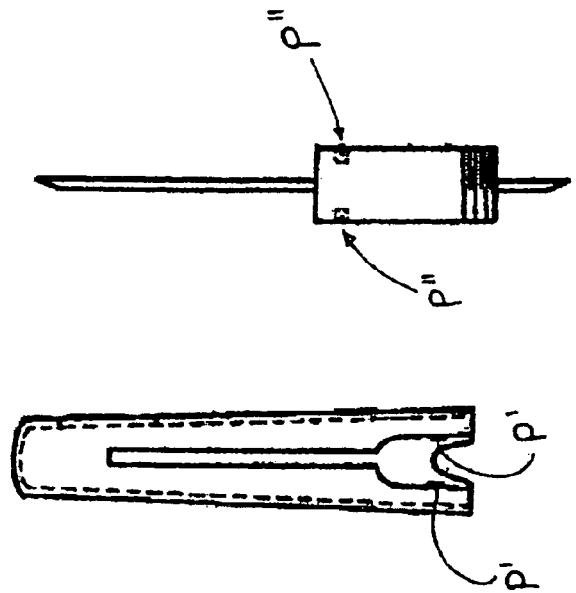
FIGS. 1 to 4 respectively show four devices for taking blood samples provided with protective shields hinged according to solutions of the prior art.
Figure 1:
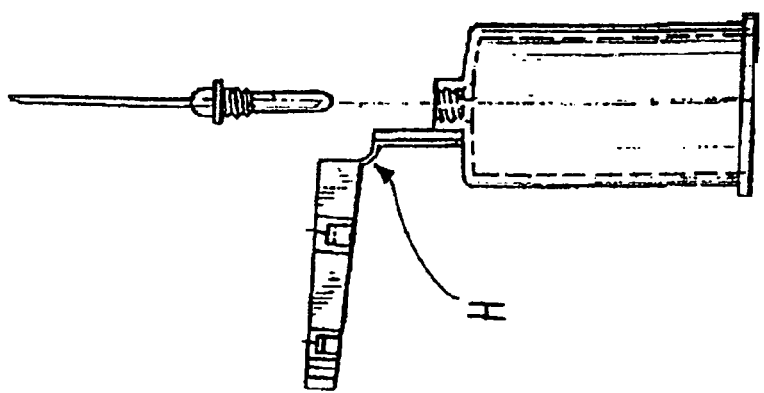
Figure 3:
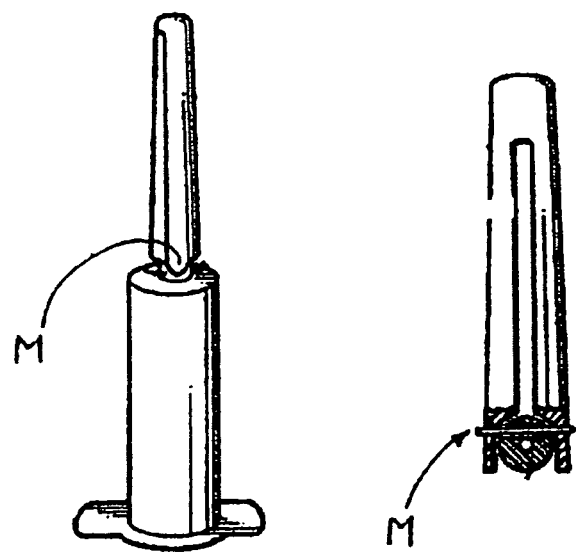
Figure 4:
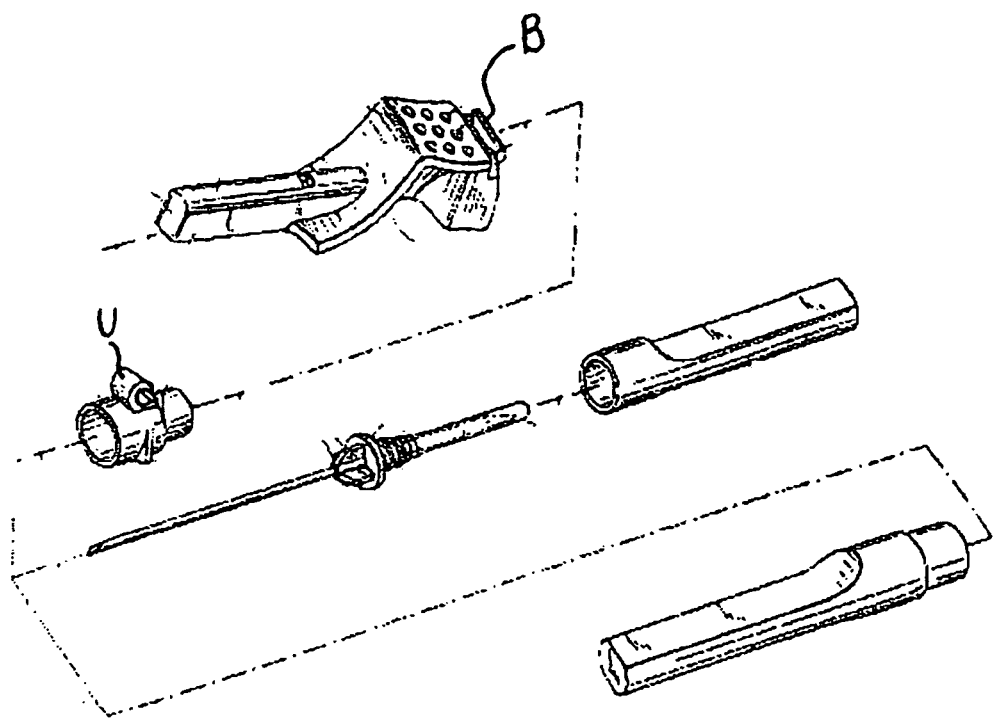
Figure 5:
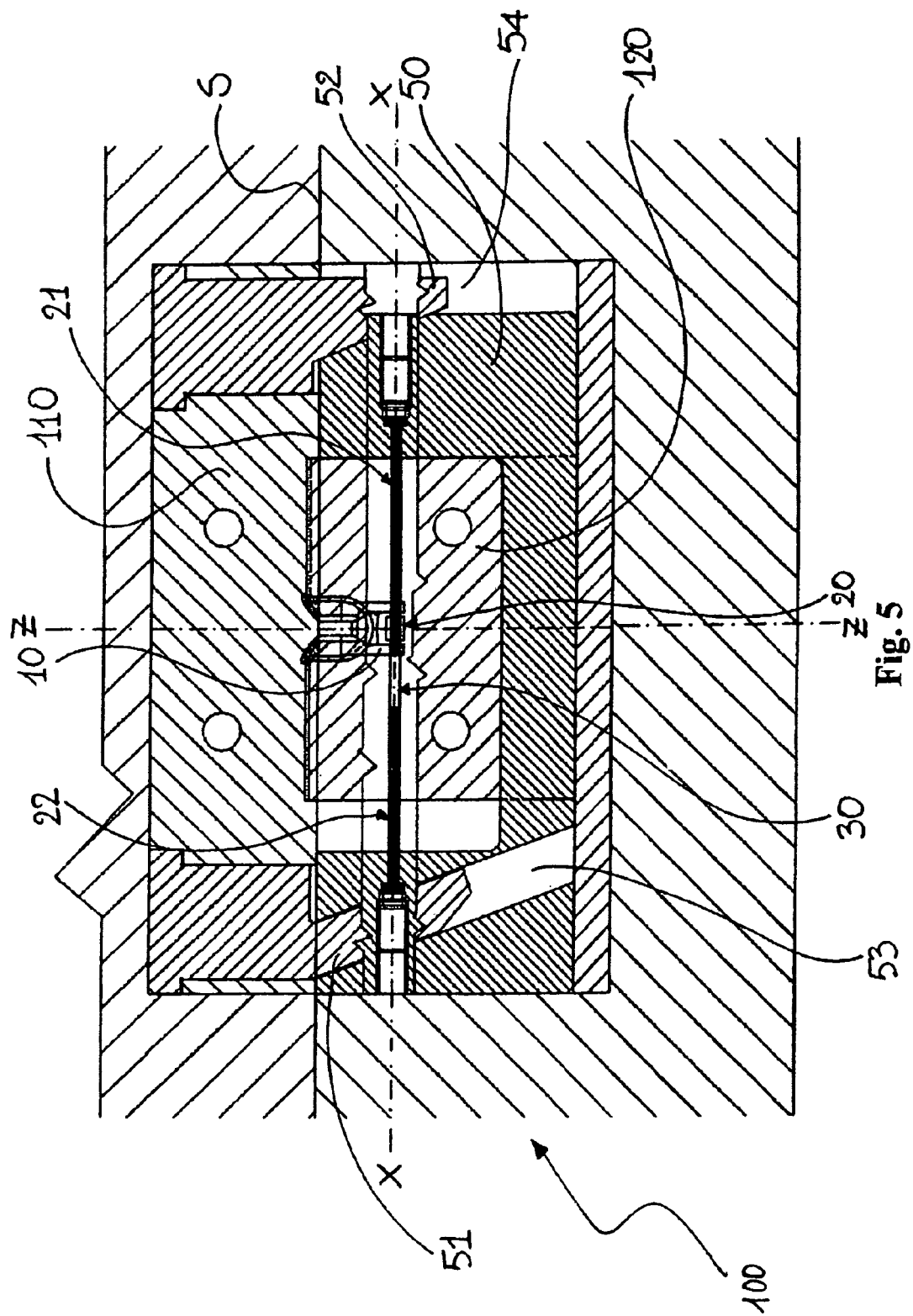
FIG. 5 shows a step of the method according to the invention relative to injecting plastic material into a mould made according to the invention.
Figure 7:
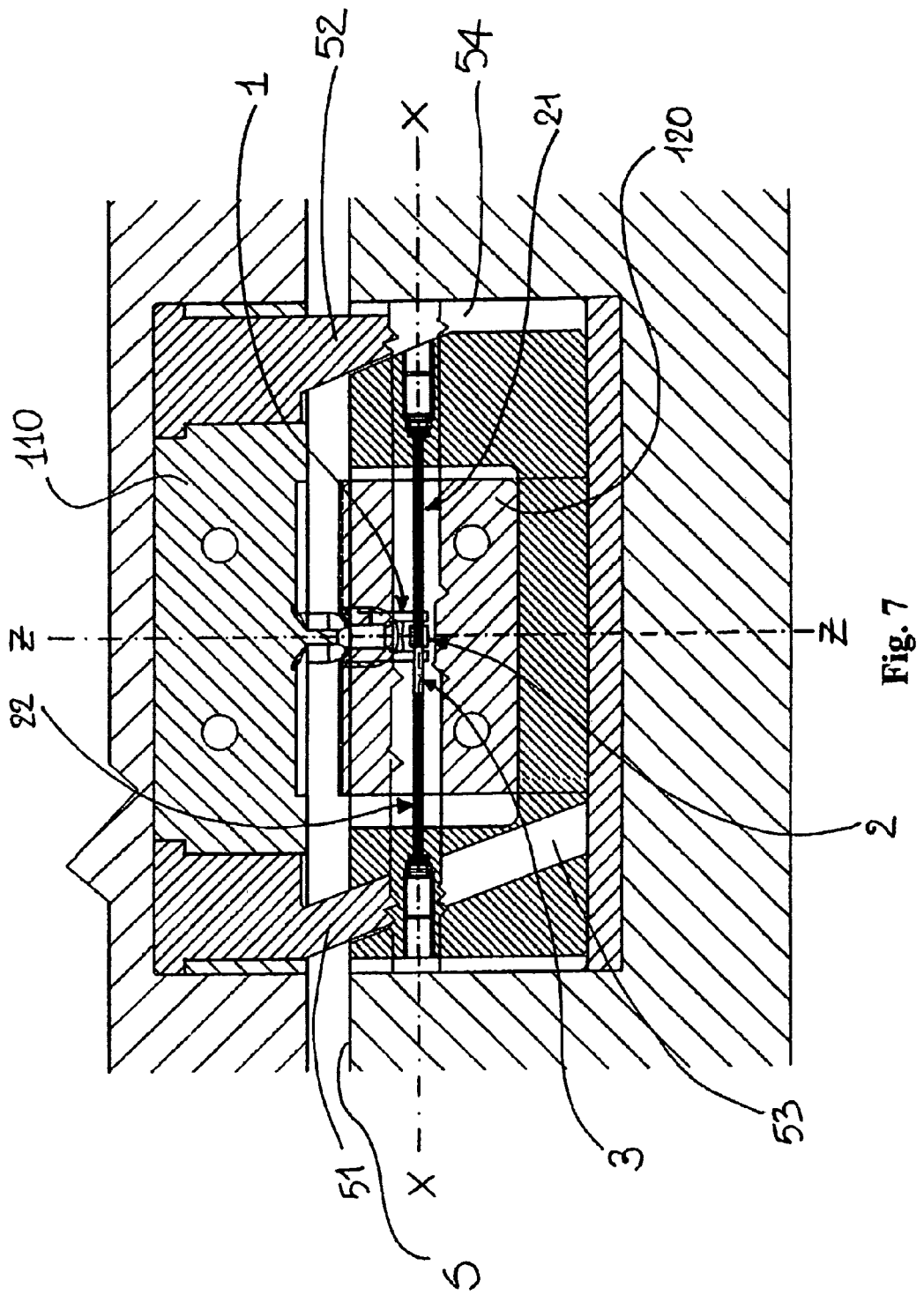
FIG. 7 shows a step of the method according to the invention relative to the insertion of a moulded pin in hinging seats provided in two other moulded portions.
Figure 8:
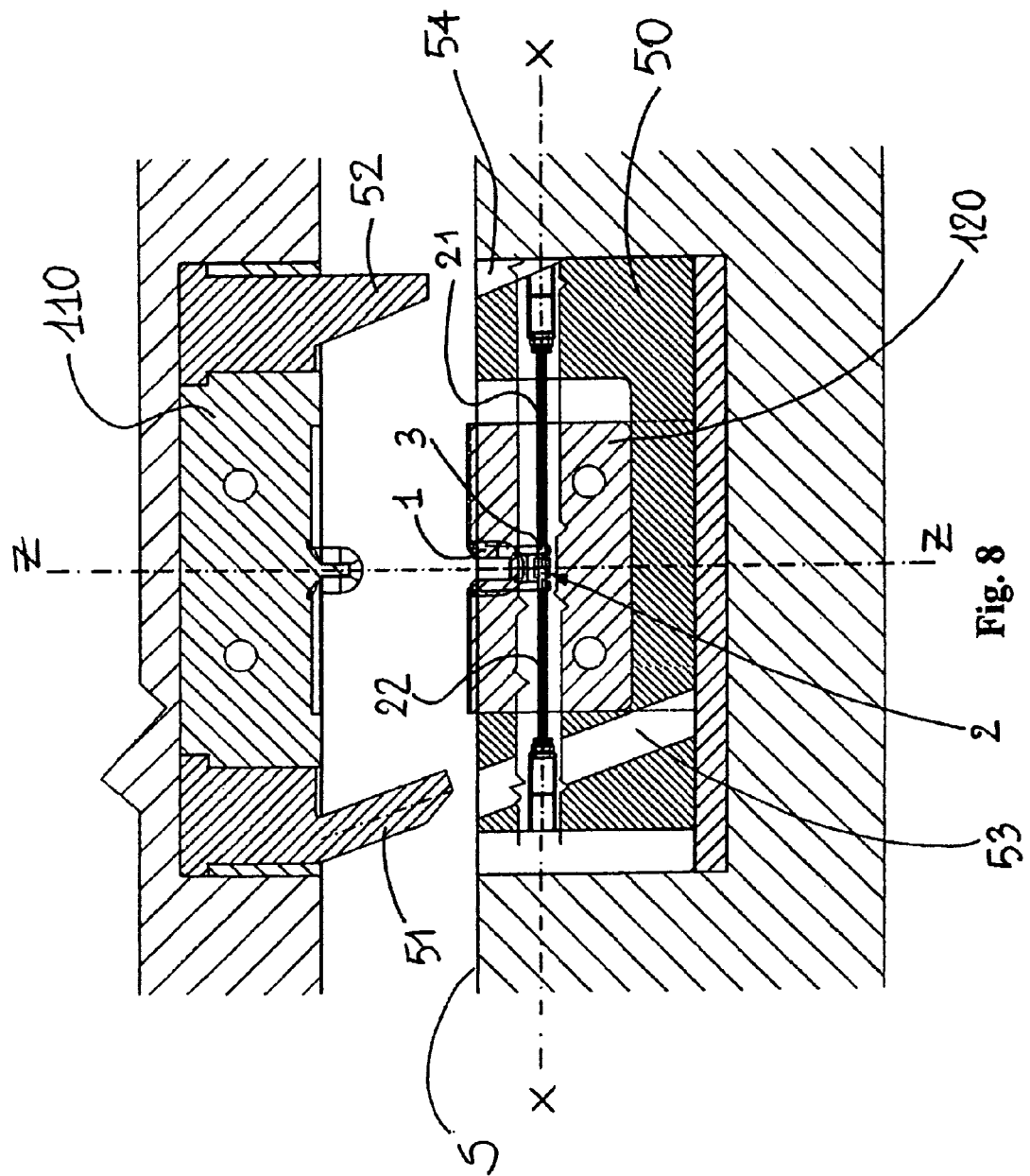
FIG. 8 shows a step of the method according to the invention relative to the complete aperture of the mould.

According to a further essential aspect of the invention, as may be seen in FIGS. 5,7 and 8, the mould 100 is provided with a pair of pegs 21, 22 which can slide along the hinge axis X between a first operating position (see FIG. 5) and a second operating position (see FIG. 8).

In their sliding motion (compare FIGS. 5, 7 and 8) the two pegs 21 and 22 remain axially distanced. The space between the two pegs 21 and 22 extends along the hinge axis X and defines the aforesaid third chamber 30.

Operatively, in the aforementioned first operating position (illustrated in FIG. 5) the first peg 21 operates as a core and contemporarily engages the first 10 and the second forming chamber 20 to define the hinging seats 14, 24 and 34 where the single pin 3 will be housed in the two portions 1 and 2. In this first position the second peg 22 is axially distanced from the first peg 22 so as to create the third chamber 30.

In the passage from the first to the second operating position (shown in FIG. 8) the second peg 22 is shifted against the two forming chambers so as to push the single pin 3 completely inside the hinging seats 14, 24 and 34. In the passage from said first to said second position, the first peg 21—keeping itself axially distanced from the second peg 22—axially disengages from the two formed portions 1 and 2, so as to free the hinging seats 14,24 and 34.

Figure 6B:
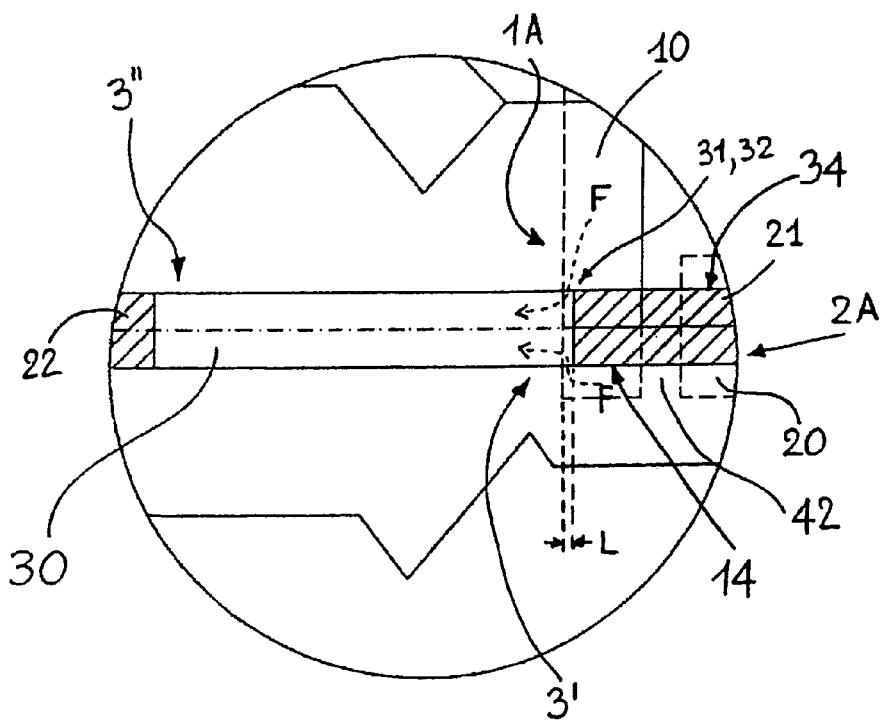
FIG. 6*b* shows an enlarged view of a detail marked by the circle in FIG. 6*a*.

Again according to the aforesaid general form of application, subsequent to step a) of predisposing the mould the method according to the invention comprises the following operating steps:

b) positioning the two pegs 21, 22 in the first operating position (see FIG. 5);

c) injecting plastic material inside the forming chambers 10,20 and 30 (see FIGS. 6a and 6b);

d) shifting the two pegs 21, 22 from the first to the second operating position (see FIGS. 7 and 8), bringing the pin 3 to engage inside the hinging seats 14, 24 and 34 thereby creating a hinge between the aforesaid two portions 1 and 2; and e) opening the mould 100 and extracting the two portions 1 and 2 already hinged to each other by the single pin 3.

Advantageously, as illustrated in detail in FIG. 15, the first and second forming chambers 10 and 20 are positioned so as to be reciprocally coupled at the portions destined to form the parts 1A, 2A which define the hinging area between the two portions 1 and 2.

Figure 16:
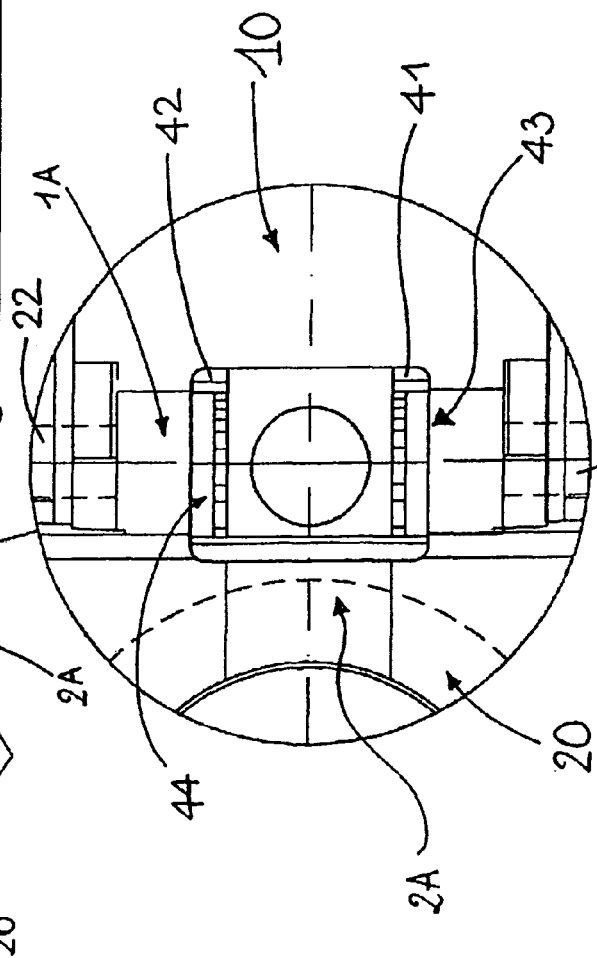
FIG. 16 is an enlarged view of a detail of FIG. 15 relative to the hinging area.

As illustrated in detail in FIGS. 6a, 6b and 16, the first and second forming chambers 10 and 20—despite being reciprocally coupled—are separated from each other by septums 41 and 42 at the parts 1A, 2A defining the hinging area.

Figure 12:
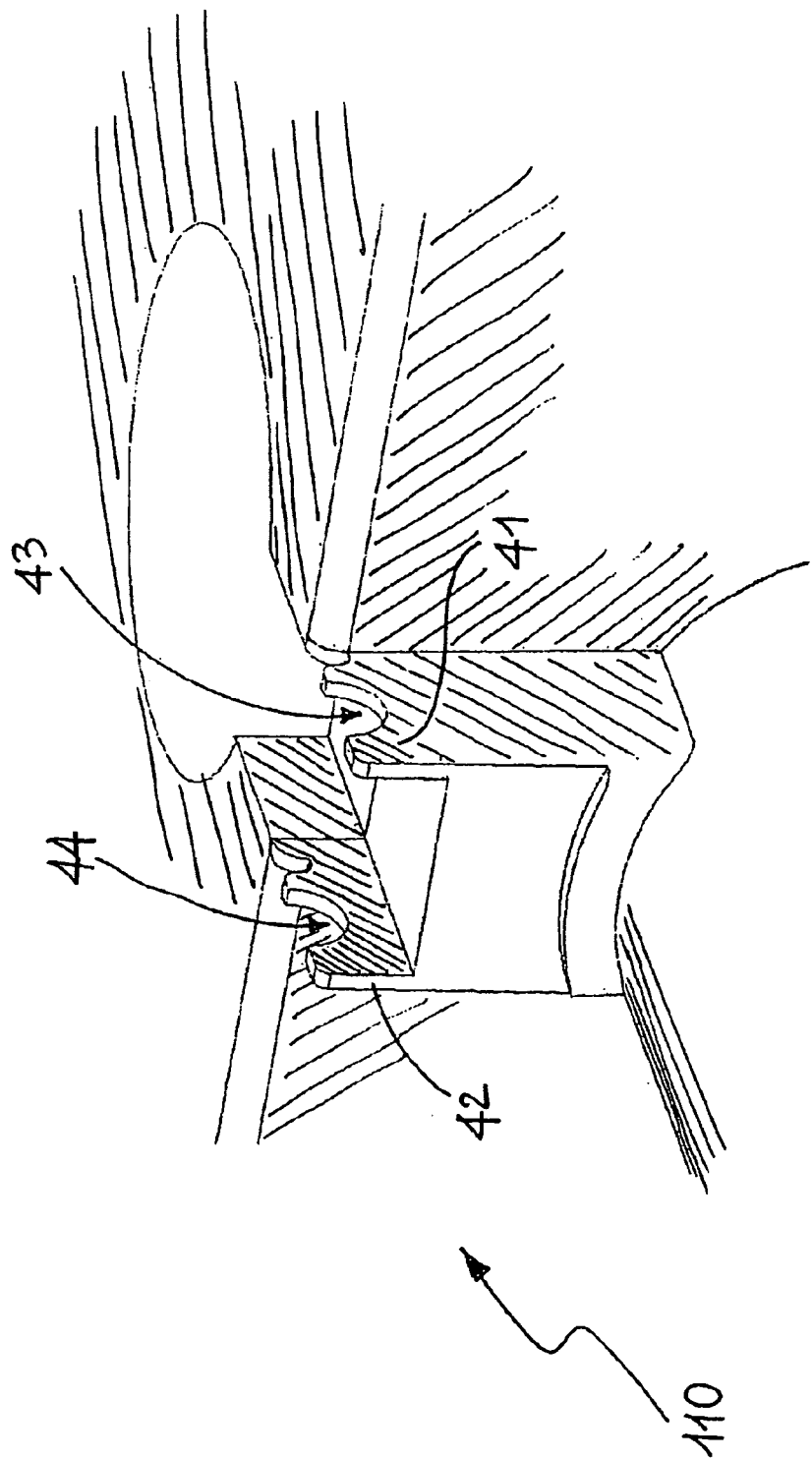
FIG. 12 shows a detail of the half mould illustrated in FIG. 11, considered from a different angle, relative to the moulding area of the hinge.
Figure 14:
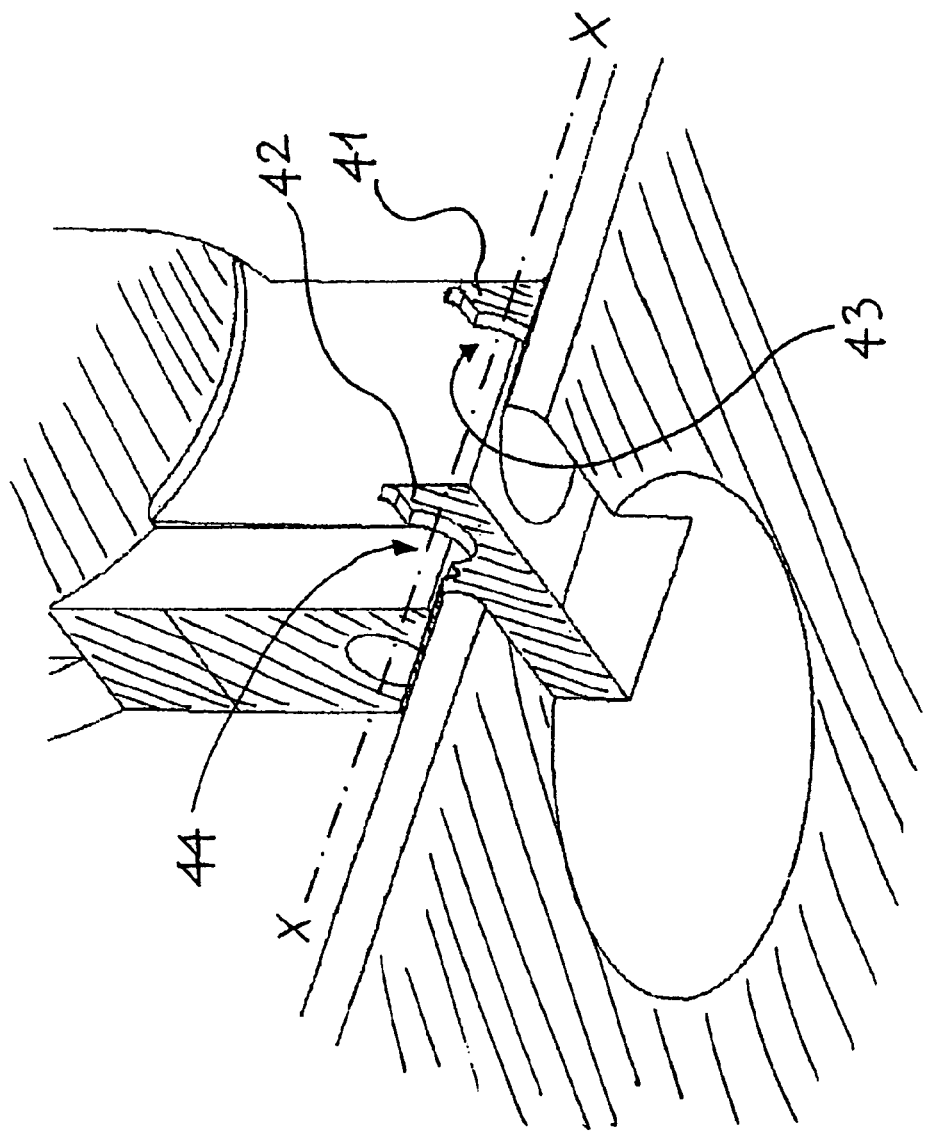
FIG. 14 shows a detail of the half mould illustrated in FIG. 13 relative to the moulding area of the hinge.

As illustrated in FIGS. 12, 14 and 16, such septums 41 and 42 are provided with axial through apertures 43, 44. Such apertures—aligned along said hinging axis X—enable the first peg 21 to engage the first two chambers 10 and 20 in the first operating position and the pin 3 to engage the hinging seats 14, 24 and 34 inserting inside them, by crossing the aforesaid septums 41 and 42.

Advantageously, the mould 100 is divided according to a separation surface S into a male half-mould 110 (see FIG. 11) and a female half-mould 120 (see FIG. 13).

Such separation surface S extends over several planes and, in particular, crosses the septums 41, 42 at the apertures 43, 44. As may be seen in particular in FIGS. 12 and 14 the apertures 43 and 44 are thus divided into two. This allows the mould to be opened when the pin 3 is inserted in the hinging seats 14.24 and 34.

According to a particularly preferred application of the invention, during the injection step c) the third forming chamber 30 is fluidically in communication with one out of the first 10 and second forming chambers 20.

Thereby making it superfluous to provide specific injection channels in the mould for the third chamber. In fact, the plastic matter injected in one of the first two chambers 10 and 20 can also fill the third chamber 30, thereby considerably simplifying the structure of the mould.

More in detail, as illustrated in FIG. 6b, the third chamber 30 is fluidically in communication with one of the other two chambers 10 and 20 at the parts 1A, 2A defining the hinging area between the two portions 1, 2 and in particular near the hinging axis X. The flow of the plastic material from one of the first two chambers 10 and 20 to the third chamber 30 is schematically illustrated in the drawing by the arrows F.

Preferably, the third chamber 30 is fluidically communicating with the first or second chamber, relative to the portion in the outermost position in the hinge.

For example, with reference to FIG. 6b, the first chamber 10 is relative to the first portion 1 (corresponding to the shield). As may be seen in FIG. 9a, the shield 1 is provided with a fork inside which an arm is inserted in an assembled condition—aligned along the hinging axis X—such arm extending from the second portion 2, corresponding to the collar. In this case the outermost portion in the hinge is the first.

With reference to FIG. 6b, the third chamber 30 is made to communicate with one of the other two chambers 10 and 20 (and in particular the one relative to the outermost portion in the hinge) by positioning the two pegs 21 and 22 appropriately along the hinging axis X.

More in detail, the first peg 21 is positioned axially so as not to fully occupy the space destined for the formation of the hinging seats. The third chamber 30 therefore extends partially inside the first chamber 10. At the head of the peg 21 a communication opening 31 is thereby created having an extension corresponding to the transversal cross section of the peg 21.

Operatively, at the end of the injection step c) the pin 3 is materially connected at a first extremity 3' to the first 1 or second portion 2 by means of a diaphragm 32 which extends all along the aforementioned communication opening 31. During the step d) of shifting the pegs 21 and 22, when the pin 3 is pushed progressively inside the hinging seats 14, 24 and 34, the aforementioned diaphragm 32 breaks under the axial thrust of the pin 3, which in turn is axially pushed by the second peg 22 at its second extremity 3".

Preferably, the aforesaid communication opening 31 has an extension L in an axial direction of 0.02 mm to 0.2 mm, and preferably of 0.05 mm.

For axial extension values L of the opening 31 of more than 0.2 mm the diaphragm which comes to be formed is too thick. Axial thrusts would therefore come to be required such as to cause a significant axial compression of the pin. As a result, the pin 3 could prove shorter than needed to the extent of invalidating the function of the hinge. In this situation there is also the risk that the fracture between the pin 3 and the portion 1 (or 2) does not follow the path ideally delimiting the communication opening 31, but rather follows an irregular path which may extend to the pin and/or to the portion 1 (or 2), affecting for example the transversal section of the pin.

For axial extension values L of the opening 31 of less than 0.2 mm, sufficient transit of molten plastic material from one of the first two chambers to the third would not be ensured with the risk therefore that the third chamber 30 would not be completely filled.

It has been seen that an axial extension L of the through opening equal to approximately 0.05 mm, is the best compromise between the two opposing requirements i.e. filling the third chamber 30 and limiting the thickness of the diaphragm 32.

The plastic material injected in the mould may be single, dual or multi-component. Co-injection may in fact be envisaged to obtain two tone or variegated colour effects or particular mechanical properties. The various moulded portions (portions 1 and 2 and the pin 3) may all be made using a single component plastic material or in differentiated materials entirely or in part, with multi-component plastic materials. In the present description and in the claims the term "plastic material" is understood to generally refer to both the case of single component plastic material or to the case of one or more multi-component materials.

Preferably, as illustrated for example in FIGS. 7 and 8, the mould 100 comprises a carriage 50 which is movably associated to the male half-mould 110 or female half mould 120 moving parallel to the hinge axis X. The carriage 50 carries the two pegs 21, 22 associated to it.

According to a preferred application of the invention, the step d) of shifting the pegs occurs contemporarily with the step e) of opening the mould 100.

Operatively, given that the movement of the pegs 21 and 22 is linked to the movement of the carriage 50, the opening of the mould 100 is designed so as to cause the movement of the carriage 50.

According to a preferred embodiment illustrated in FIGS. 5 to 8, the mould 100 comprises coupling appendages 51, 52 between the two half-moulds 110, 120. When the mould is closed (see FIG. 5) such appendages 51, 52 are inserted in slide seats 53, 54 made on the carriage 50.

More in detail, such slide seats 53, 54 are inclined in relation to the opening direction Z of the mould (substantially orthogonal to the X axis) so that during the opening step e) of the mould the aforesaid appendages 51 and 52, progressively extracted from the slide seats 53 and 54, impress on the carriage 50 and on the associated pegs 21 and 22 an axial movement so as to move the pegs from the first to the second operating position.

As already mentioned above, the pin 3 needs to be able to work with an interference relation at least with some sections of the hinge seats 14, 24 and 34. The interference is essential for preventing the pin 3 from accidentally coming out of the hinging seat and for the shield to rotate freely around the pin by gravity, under its own weight, thereby preventing normal use of the device itself.

Advantageously, thanks to the method according to the invention, the dimensions of the pin 3 can be adapted depending on the final mechanical characteristics which the hinge must have.

In particular the size of the pin and/or hinge seats can be scaled so as to make the movement of the hinge more or less resistant.

According to a particular embodiment, the pin is made so as to obtain a hinge with totally free movement. In other words, the two portions are free to rotate with each other. In this case the pin 3 works with an interference relation with only one of the two portions so as to prevent the risk of coming out of the seat. Between the pin and the other portion however there is play.

According to an alternative embodiment, the pin is made so as to obtain a hinge suitable for allowing a controlled rotation movement. In other words, the reciprocal rotation between the two portions is not free, there being friction between the pin and the hinge seats. In this case the pin 3 is substantially blocked in the seats made in one portion, while it can rotate—albeit in a controlled manner—inside the seats in the other portion.

As already mentioned, the method according to the invention, can be used to simply and economically produce needle protection devices associable to vial holders or protected needle holder devices associated to vial holders, comprising portions mechanically hinged to each other by a single pin, having full operative functionality. Devices overcoming all the limitations of the prior art mentioned above are thereby obtained.

Figure 9A:
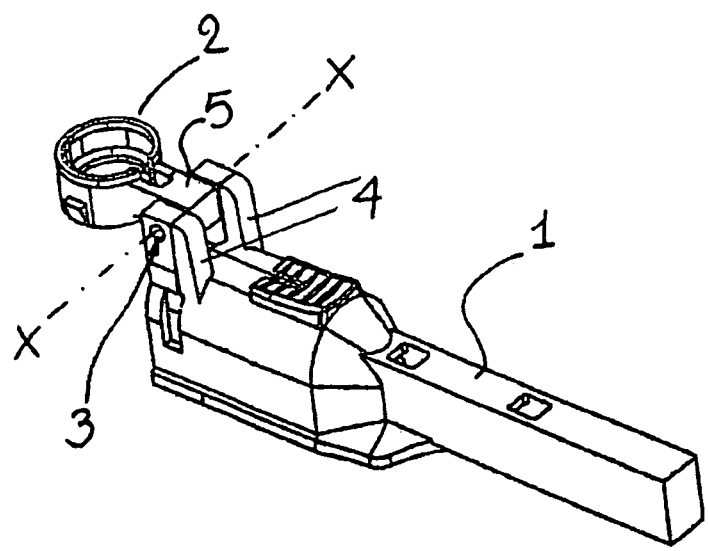
FIG. 9*a* shows a protective shield for needles provided with a collar hinged to it, made according to the invention.
Figure 9B:
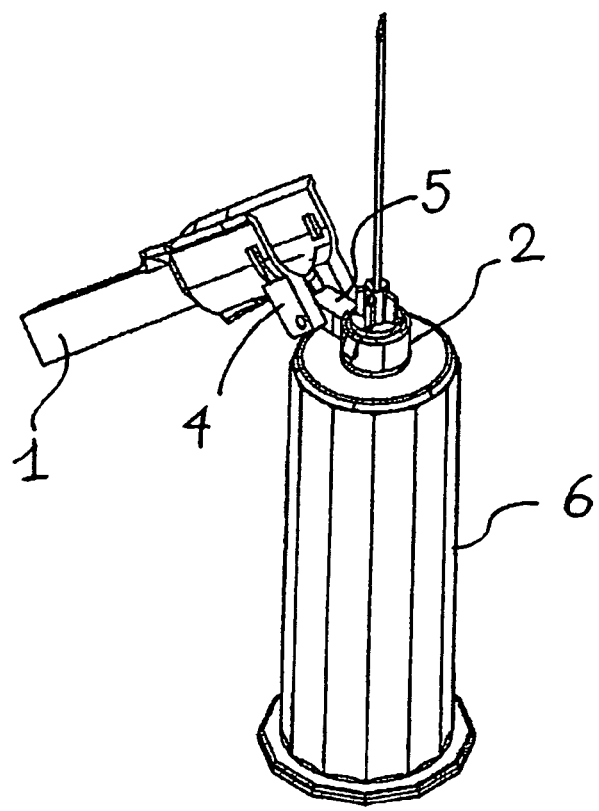
FIG. 9*b* shows the protective shield and relative collar illustrated in FIG. 9*a* associated to a vial holder.

FIGS. 9a and 9b illustrate a needle protection device for vial holders made using the production method according to the invention.

More in detail, the device comprises a protective shield 1 (corresponding to portion 1) hinged by a single pin 3 to a collar 2 (corresponding to the portion 2). The device is destined to be associated to the neck of a vial holder 6 by means of the aforesaid collar 2, as illustrated in FIG. 9b.

Advantageously, the shield 1 and the collar 2 are respectively provided with a first 4 and a second 5 projecting extension, mechanically coupled to each other in mutual rotation by the single pin 3 inserted in the hinge seats 14, 24, 34 made in the aforesaid extensions 4, 5.

In particular the first extension 4 comprises two parallel arms distanced from each other; the second extension comprises, rather, a single arm destined to be inserted between the two arms of the first extension.

Figure 10:
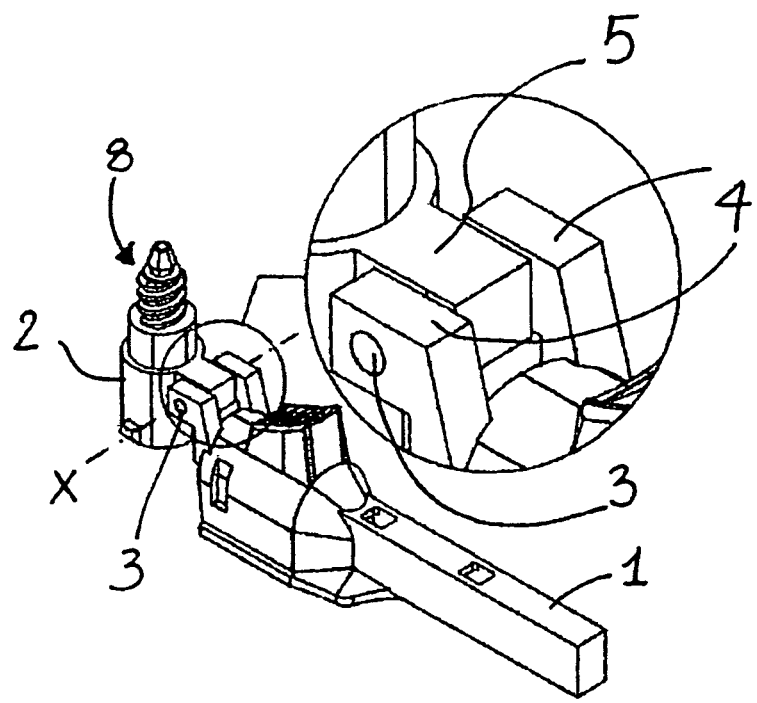
FIG. 10*a* shows a needle holder hub provided with a protective shield hinged to it, made according to the invention.
FIG. 10*b* shows the needle holder hub and relative collar illustrated in FIG. 10*a* associated to a dual tip needle.
Figure 10:
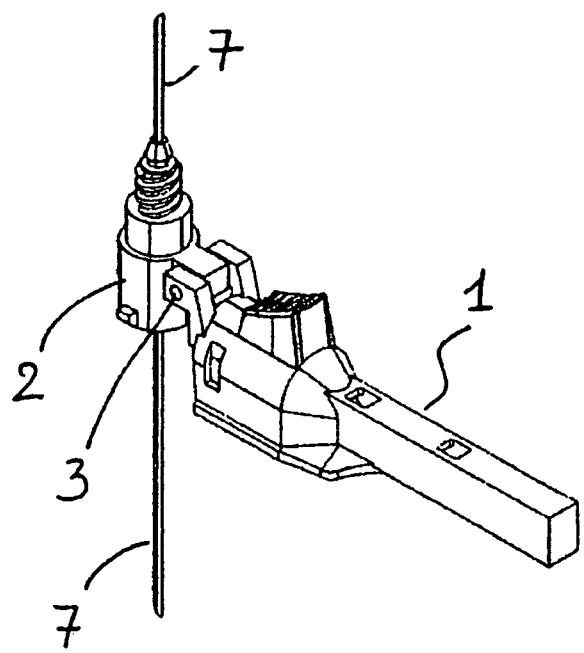

FIGS. 10a and 10b illustrate a needle protection device associable to a vial holder made using the production method according to the invention.

More in detail, the device comprises a hub 2 (corresponding to the portion 2) and a protective shield 1 (corresponding to the portion 1) hinged to the hub 2 by a single rotation pin 3.

The hub is destined to receive in an axial position a dual tip needle 7, as illustrated in FIG. 10b. The hub 2 is provided with a thread part 8 for connection to a vial holder.

Similarly to the device illustrated in FIGS. 9a and 9b, the shield 1 and the hub 2 are respectively provided with a first 4 and a second 5 projecting extension, mechanically coupled to each other in reciprocal rotation by the single pin 3 inserted in the hinge seats 14, 24, 34 made in the aforesaid extensions 4,5.

In particular the first extension 4 comprises two parallel arms distanced from each other; the second extension comprises, rather, a single arm destined to be inserted between the two arms of the first extension.

The present invention enables numerous advantages to be achieved, some of which mentioned above.

The method according to the invention, makes it possible to simply and economically produce bodies in plastic material (in particular needle protection devices for clinical use) comprising portions mechanically hinged to each other by a single pin, having full operative functionality.

Thanks to the method according to the invention, the production process is significantly simplified given that the assembly of the single components takes place contextually with the injection moulding of the said components. Handling of small sized components is therefore no longer required.

The method according to the invention, also makes it possible to achieve the mechanical interference couplings of a number of parts of a small size automatically.

The method further enables varying of the hinge characteristics, passing from a freely moving hinge to a hinge having a controlled movement.

The method according to the invention, in particular makes it possible to produce needle protection devices or protected needle holder devices—provided with a rotating shield—which combine easy and simple production with full and safe operating functionality.

Contrary to the prior art, thanks to the method according to the invention, it is in fact possible to produce a blood sampling device provided with a protective shield rotating by means of a stable and functional mechanical joint during the rotation movement of the pin itself.

The invention thus conceived thereby achieves the intended purposes.

Obviously, it may assume, in its practical embodiments, forms and configurations different from those illustrated above while remaining within the present sphere of protection.

Furthermore, all the parts may be replaced with technically equivalent parts and the dimensions, shapes and materials used may be varied as required.

The invention claimed is:

1. Method for the production of bodies in plastic material comprising at least two portions hinged to each other by a single rotation pin extending along a hinge axis, said method comprising the following steps:
   a) predisposing a mold provided with at least two distinct forming chambers for forming said two portions, said chambers being shaped so that said two portions are formed already positioned in a position of reciprocal coupling, said mold comprising a third forming chamber for forming said single pin, said third chamber being made in such a way that said pin is formed aligned along the hinge axis, said mold being provided with a pair of pegs which are slidable along said hinge axis between a first and a second operating position, said pegs having a distance therebetween forming said third chamber, in said first operating position a first peg operating as a core to define hinging seats in said two portions and in said second operating position a second peg operating as a pusher for said single pin inside said seats;
   b) positioning said pegs in said first operating position;
   c) injecting plastic material inside said forming chambers;
   d) shifting said pegs from said first to said second operating position, bringing said pin to engage inside said seats thereby creating a hinge between said two portions; and
   e) opening said mold and extracting said two portions hinged to each other by said single pin.

2. Method according to claim 1, wherein said first and said second forming chambers are separated from each other by septums at the parts defining the hinging area between said two portions.

3. Method according to claim 1, wherein said first and said second forming chambers are separated from each other by septums at the parts defining the hinging area between said two portions, said septums being provided with through apertures for said first peg aligned along said hinge axis.

4. Method according to claim 3, wherein said mold is divided according to a separation surface into a male half-mold and a female half-mold, said surface dividing said septums at said apertures.

5. Method according to claim 1, wherein during said injection step said third forming chamber is fluidically communicating with one of said first and said second chambers.

6. Method according to claim 1, wherein during said injection step said third forming chamber is fluidically communicating with one of said first and said second chambers, said third chamber being fluidically communicating with one of said first and said second chambers at the parts which define the hinging area between said two portions.

7. Method according to claim 1, wherein during said injection step said third forming chamber is fluidically communicating with one of said first and said second chambers, the communication opening between said third chamber and said first or second chamber having an extension in an axial direction ranging from 0.02 mm to 0.2 mm, and preferably of 0.05 mm.

8. Method according to claim 7, wherein at the end of the first injection step c) said pin is connected to said first or to said second portion via a diaphragm which extends in said communication opening, said diaphragm breaking in said step of shifting of the pegs when said pin is progressively pushed inside said hinging seats.

9. Method according to claim 1, wherein said shifting step d) of the pegs occurs contemporaneously with said opening step e) of the mold.

10. Method according to claim 1, wherein said mold comprises a carriage associated with said male half-mold or said female half-mold, said carriage carrying said two pegs associated to it, and being mobile parallel to said hinge axis.

11. Method according to claim 1, wherein said shifting step d) of the pegs occurs contemporaneously with said opening step e) of the mold and said mold comprises a carriage associated with said male half-mold or said female half-mold, said carriage carrying said two pegs associated to it, and being mobile parallel to said hinge axis, wherein said mold comprises coupling appendages between said two half-molds which when the mold is closed are inserted in slide seats made on said carriage, said seats being inclined in relation to the direction in which the mold opens in such a way that during said opening step e) of the mold said appendages, progressively extracted from said seats, impress on said carriage and on the associated pegs an axial movement.

12. Injection mold of plastic material to form at least two portions hinged to each other by a single rotation pin extending along a hinge axis, same mold comprising
   at least two distinct forming chambers for forming said two portions, said chambers being shaped so that said two portions are formed already positioned in a position of mutual coupling,
   a third forming chamber for forming said single pin, said third chamber being made in such a way that said pin is formed already along the hinge axis, and
   said mold further comprising a pair of pegs sliding along said hinge axis between a first and a second operating position, said pegs having a distance therebetween forming said third chamber, in said first operating position a first peg operating as a core to define hinge seats in said two portions, and in said second operating position a second peg acting as a pusher for said single pin inside said seats.

13. Mold according to claim 12, wherein said first and said second forming chamber are separated from each other by septums at the parts defining the hinging area between said two portions.

14. Mold according to claim 12, wherein said first and said second forming chambers are separated from each other by septums at the parts defining the hinging area between said two portions and wherein said septums are provided with through apertures for said first peg aligned along said hinge axis.

15. Mold according to claim 12, wherein said first and said second forming chambers are separated from each other by septums at the parts defining the hinging area between said two portions and wherein said mold is divided according to a separation surface into a male half-mold and a female half-mold, said surface dividing said septums at said apertures.

16. Mold according to claim 15, wherein, when the mold is closed, said third forming chamber is fluidically communicating with one of said first and said second chambers.

17. Mold according to claim 15, wherein, when the mold is closed, said third forming chamber is fluidically communicating with one of said first and said second chamber, and wherein said third chamber is fluidically communicating with one of said first and said second chambers at the parts which define the hinging area between said two portions.

18. Mold according to claim 15, wherein, when the mold is closed, said third forming chamber is fluidically communicating with one of said first and said second chamber, and wherein the communication opening between said third chamber and said first or second chamber has an extension in an axial direction ranging from 0.02 mm to 0.2 mm, and preferably of 0.05 mm.

19. Mold according to claim 12, wherein said first and said second forming chamber are separated from each other by septums at the parts defining the hinging area between said two portions and said mold is divided according to a separation surface into a male half-mold and a female half-mold, said surface dividing said septums at said apertures, said mold comprising a carriage associated with said male half-mold or said female half-mold, said carriage carrying said two pegs associated to it, and being mobile parallel to said hinge axis.

20. Mold according to claim 19, comprising coupling appendages between said two half-molds which, when the mold is closed, are inserted in slide seats made on said carriage, said seats being inclined in relation to the direction in which the mold opens, in such a way that during said opening step of the mold said appendages, progressively extracted from said seats, impress on said carriage and on the associated pegs an axial movement.

* * * * *